United States Patent
Cotte

(10) Patent No.: US 10,847,755 B2
(45) Date of Patent: Nov. 24, 2020

(54) METHOD FOR PRODUCING A DISPLAY DEVICE, AND DISPLAY DEVICE

(71) Applicant: PA.COTTE Family Holding GmbH, Amberg (DE)

(72) Inventor: Pierre-Alain Cotte, Amberg (DE)

(73) Assignee: PA.COTTE FAMILY HOLDING GMBH, Amberg (DE)

( * ) Notice: Subject to any disclaimer, the term of this patent is extended or adjusted under 35 U.S.C. 154(b) by 63 days.

(21) Appl. No.: 16/081,555

(22) PCT Filed: Mar. 2, 2016

(86) PCT No.: PCT/EP2016/000365
§ 371 (c)(1),
(2) Date: Aug. 31, 2018

(87) PCT Pub. No.: WO2017/148491
PCT Pub. Date: Sep. 8, 2017

(65) Prior Publication Data
US 2020/0067021 A1    Feb. 27, 2020

(51) Int. Cl.
*H01L 51/52* (2006.01)
*A61B 5/01* (2006.01)
(Continued)

(52) U.S. Cl.
CPC ............ *H01L 51/5262* (2013.01); *A61B 5/01* (2013.01); *A61B 5/02055* (2013.01);
(Continued)

(58) Field of Classification Search
None
See application file for complete search history.

(56) References Cited

U.S. PATENT DOCUMENTS 6,636,185 B1    10/2003    Spitzer et al.
7,576,915 B2    8/2009    Kurt
(Continued)

FOREIGN PATENT DOCUMENTS

EP            992833 A2        4/2000
JP        2008/134318 A        6/2008
(Continued)

OTHER PUBLICATIONS

European Patent Office, International Preliminary Report on Patentability for PCT Application No. PCT/EP2016/000365 dated Sep. 4, 2018.
(Continued)

*Primary Examiner* — Steven M Christopher
(74) *Attorney, Agent, or Firm* — Social IP Law Group LLP; Angelo Gaz

(57) ABSTRACT

The invention relates to a method for producing a thin and substantially fracture-resistant display device comprising a display, wherein an upper layer having a surface facing an observer is arranged on light-emitting luminous surfaces of the display, wherein micro-passages for transmitting generated light from the light-emitting luminous surfaces of the display are formed in the upper layer and form micro-openings in the surface facing an observer, wherein a substantially planar surface facing the observer is created on the upper layer, and wherein creating the substantially planar surface comprises processing the surface of the display device facing the observer by means of a laser and/or by means of machining in order to produce the substantially planar surface. Furthermore, the invention relates to a display device.

5 Claims, 5 Drawing Sheets

(51) Int. Cl.
| | |
|---|---|
| A61B 5/0205 | (2006.01) |
| A61B 5/00 | (2006.01) |
| G10K 15/04 | (2006.01) |
| G10L 25/51 | (2013.01) |
| H01L 23/34 | (2006.01) |
| H01L 27/32 | (2006.01) |
| H01L 51/56 | (2006.01) |
| H01S 5/42 | (2006.01) |
| A61B 5/024 | (2006.01) |
| G01N 33/00 | (2006.01) |
| G02B 27/09 | (2006.01) |

(52) U.S. Cl.
CPC ............ *A61B 5/742* (2013.01); *A61B 5/748* (2013.01); *G10K 15/04* (2013.01); *G10L 25/51* (2013.01); *H01L 23/34* (2013.01); *H01L 27/322* (2013.01); *H01L 27/323* (2013.01); *H01L 27/3225* (2013.01); *H01L 27/3227* (2013.01); *H01L 51/5253* (2013.01); *H01L 51/5284* (2013.01); *H01L 51/56* (2013.01); *H01S 5/423* (2013.01); *A61B 5/02438* (2013.01); *A61B 2560/0214* (2013.01); *A61B 2562/0247* (2013.01); *A61B 2562/0271* (2013.01); *A61B 2562/12* (2013.01); *G01N 33/0062* (2013.01); *G02B 27/09* (2013.01)

(56) References Cited

U.S. PATENT DOCUMENTS

| | | | |
|---|---|---|---|
| 9,318,428 | B2 | 4/2016 | Scheucher |
| 2003/0025849 | A1 | 2/2003 | Hara |
| 2007/0075471 | A1 | 4/2007 | Kuehnle et al. |
| 2007/0138951 | A1 | 6/2007 | Park et al. |
| 2007/0222922 | A1 | 9/2007 | Jin et al. |
| 2008/0024470 | A1 | 1/2008 | Andre et al. |
| 2011/0157887 | A1* | 6/2011 | Jeong .................. H01L 51/5271 362/235 |
| 2011/0193824 | A1 | 8/2011 | Modarres et al. |
| 2013/0099839 | A1 | 4/2013 | Kao et al. |
| 2014/0354927 | A1* | 12/2014 | Kanno ................ G02B 5/0257 349/112 |
| 2017/0076693 | A1* | 3/2017 | Cotte ...................... G09G 3/36 |

FOREIGN PATENT DOCUMENTS

| | | |
|---|---|---|
| WO | 2005/059636 A1 | 6/2005 |
| WO | 2013/117760 A1 | 8/2013 |
| WO | 2017/148491 A1 | 9/2017 |

OTHER PUBLICATIONS

Füssel et al., Fertigungstechnik, Dec. 1, 2014, pp. 2-10.
Chiseki et al., Nanostructure array fabrication, American Institute of Physics, Nov. 17, 1997, pp. 2934-2936.
Erich Müller, Focused-Ion-Beam, Jun. 4, 2012, pp. 1-2.
COTEC GmbH, Nanotechnologie, May 18, 2011, pp. 1-2.
European Patent Office, ISA, International Search Report for PCT Application no. PCT/EP2016/000365 dated Mar. 13, 2017.
European Patent Office, ISA, Written Opinion for PCT Application No. PCT/EP2016/000365 dated Mar. 13, 2017.

* cited by examiner

METHOD FOR PRODUCING A DISPLAY DEVICE, AND DISPLAY DEVICE

CROSS-REFERENCE TO RELATED APPLICATIONS INFORMATION

This patent claims priority to PCT Application PCT/EP2016/000365 filed Mar. 2, 2016 entitled METHOD FOR PRODUCING A DISPLAY DEVICE, AND DISPLAY DEVICE.

The invention relates to a method for producing a thin and substantially fracture resistant display device with a display, wherein an upper layer is arranged over light-emitting luminous areas of the display, said upper layer having a surface facing a viewer. Further the invention relates to a display device.

Display devices with a surface made of glass facing a viewer are known in the prior art e.g. as LCD display devices or OLED display devices, in particular for tablets or mobile phones. Disadvantages of such display devices are the limited contrast range that these display devices have, as well as the necessary thickness of the protective glass of these display devices.

Therefore the present invention addresses the problem of improving a method for producing a display device with a display with several pixels or light-emitting luminous areas, e.g. LCD- or OLED display devices, with respect to the contrast ranges and/or with respect to the display quality and/or with respect to the visual impression of such a display and/or designing the display device more fracture behavior efficient and/or optimizing the weight of a display device and/or improving the mechanical stability.

This problem is solved by the independent claims. Advantageous improvements are defined in the dependent claims.

In particular the problem is solved by means of a method for producing a thin and substantially fracture resistant display device with a display.

In the process the method preferably comprises the fact that an upper layer is arranged over light-emitting luminous areas of the display, said upper layer having a surface facing a viewer, wherein preferably the upper layer comprises substantially metal and/or a non-transparent and/or a non-light reflecting material. In the process the upper layer can be arranged directly or indirectly at light-emitting luminous areas of the display. As a result, not only does the method for producing a display differ in principle from conventional manufacturing methods, rather the manufactured display device also differs. This is because, while conventional display devices have an upper layer substantially consisting of glass, which allows the light from a display to pass to a viewer,—expressed in simplified terms—this transparent glass layer from the prior art can be replaced by a substantially non-transparent upper layer made of metal and/or by a non-transparent and/or non-light reflecting material. The advantage in replacing the glass with metal and/or a non-transparent and/or non-light reflecting material lies first of all in the fact that for example metal has a significantly higher mechanical stability than glass, in particular with respect to the fracture resistance.

In the present description a "display" preferably means an electrically controlled display without movable parts for optical signaling of variable information like images or characters. Ideally the variable information like images or characters is produced from a plurality of light-emitting luminous areas, which preferably can also produce different colors.

An upper layer, which "comprises substantially metal and/or a non-transparent and/or non-light reflecting material", in the present description preferably means that the upper layer has a fracture behavior, that preferably approximates a metal or a plastic, or that the upper layer has a ductile behavior, in particular of a plastic or a metal. In particular an upper layer, which has "substantially metal and/or a non-transparent and/or non-light reflecting material", preferably means a layer, which contains metal and/or a non-transparent and/or non-light reflecting material of at least 2%, in particular 5% of the material. The higher the percentage of the metal, of the non-transparent and/or non-light reflecting material the higher the mechanical stability against breakage or the higher the fracture resistance of the upper layer. Therefore an upper layer, that comprises metal and/or a non-transparent and/or non-light reflecting material to at least 90%, is especially preferable, since such an embodiment virtually corresponds to the material properties of a metal, of a non-transparent and/or non-light reflecting material.

Metal has the advantage that it—depending on embodiment—has a high surface strength against outer influences, such as such as scratches or impacts. It also withstands outer mechanical influences, such as falls, due to a high elasticity limit or due to plastic deformation.

Advantageously the non-transparent material is a plastic, in particular a ductile plastic, which deforms elastically first and does not break until after plastic deformation. In this way the display device can have the best possible protection from outer mechanical influences, such as falls. It is also favorable, if the non-transparent material can compensate for mechanical influences with a high elasticity limit.

In addition, it is favorable if the non-light reflecting material is a material, in particular a plastic, which additionally favorably has ductile properties, in order to allow an elastic expansion/deformation and to break only after a plastic deformation. Also, the non-light reflecting material has the advantage that incident light does not produce any disturbing light reflections, which impede the viewer of a display device when viewing. In addition, it is advantageous in a further step of the method that in the upper layer micro-passages are formed for letting through generated light of the light-emitting luminous areas of the display, which form micro-openings in the surface facing a viewer. Thus light from light-emitting luminous areas of a display can penetrate through the upper layer or through the micro-passages and exit at the micro-openings of the surface of the display device facing a viewer. In the process the upper layer comprises—as already mentioned—a preferably non-transparent material, such as e.g. metal. With the assistance of the embodiment of the upper layer as a—expressed in other words—perforated layer it is possible to create an improved contrast, in particular an improved black contrast. In combinations of the micro-passages with the upper layer, which preferably has substantially metal or a non-transparent or a non-light reflecting material, thus in addition a reinforced, thinner display device is created with improved contrast.

Preferably the micro-openings are introduced on the surface of the upper layer facing a viewer with a percentage of less than 10% of the total surface of the upper layer facing the viewer. In other words, it is preferred that micro-passages are introduced in the upper layer, which allow light to pass through that is produced on the one side of the upper layer and is emitted on the other side of the upper layer. In the process, preferably the generated light exits the micro-openings in the surface of the upper layer facing a viewer and can thus reach a viewer. On the basis of the preferred circumstance that the percentage of the micro-openings of the total surface of the upper layer facing the viewer is less than 10%, a substantially or to a large extent closed surface of a display device can be ensured, which preferably has a high measure of fracture resistance, if it is realized with a ductile material, such as e.g. metal. Also, with the help of the mentioned embodiment a higher contrast range or a higher contrast value/contrast can be produced.

Preferably the distances between two micro-openings are smaller than the resolution capacity of the viewer. In the process, these are distances, which appear to the viewer at an angle of a maximum of two angular minutes. As a result pixel or micro-openings are no longer distinguishable for a majority of viewers, because the human resolution capacity in unfavorable cases corresponds to roughly two angular minutes.

Especially preferably, the distances of the micro-openings appear to the viewer at a maximum angle of 1 angular minute, especially preferably 0.5 angular minutes, especially preferably 0.25 angular minutes. As a result, pixel or micro-openings are no longer distinguishable for virtually all human viewers. The smaller the maximum angle, the fewer viewers exist, whose eyesight suffices for distinguishing two pixels or micro-openings or luminous areas.

Preferably the eye or eyes of the viewer have a distance to the display area, which is common for the concrete type of display device in the use of the display device. For example, the distance is 5 cm to 1.20 m, preferably 15 cm to 60 cm for displays of handheld devices (mobile phones, watches, tablet computers), 25 cm to 2 m, preferably 40 cm to 1 m for displays of desktop computers, 1 m to 7 m preferably 2 m to 5 m for television sets and/or 2 m to 100 m, preferably 5 m to more than 100 m for advertisement and information displays. Especially preferably are distances that are smaller than the resolution capacity of the viewer, e.g. smaller than 30 μm (800 to 1000 DPI (dots per inch) for small devices or e.g. a distance in the case of a television smaller than 0.5 mm, in which the user at a conventional viewing distance (>2 m) can then no longer distinguish the individual pixels or micro-openings or luminous areas from one another.

For example, the display device is a desktop computer with a minimum user distance (with reference to the eye) of 50 cm. In the hypothetical assumption that e.g. 70% of potential users do not have better resolution capacity than 0.6 angular minutes, the pixel or micro-openings or luminous areas of the display device are spaced apart from one another less than or equal to 87 μm, preferably 80 μm for a safety buffer, so that for at least 70% of users in the case of normal usage of the display device an especially high-value display is made possible, since for them individual luminous areas or micro-openings are not distinguishable. A resolution of the display device of 317 DPI results, preferably 320 DPI with error margin.

Preferably the distances, which are smaller than the resolution capacity of the viewer, are a maximum of 190 μm, preferably a maximum of 80 μm, especially preferably a maximum of 50 μm. As a result, even if the viewer of the display area comes closer than usual, said viewer cannot distinguish individual pixels or micro-openings or luminous areas from one another. Depending on resolution capacity and accommodative capacity of the individual viewer it is thus even unimportant how close the individual viewer of the display device comes, because said viewer, even in the case of optimum utilization of his or her eyesight and an approach to the closest focusing distance of his/her eye can scarcely differentiate the individual pixels or micro-openings or luminous areas from one another.

Preferably the extension of one, preferably every, micro-opening or luminous area is at the most by 70 μm, preferably at the most by 25 μm, especially preferably at the most by 10 μm or even at the most by 5 μm. As a result the viewer cannot detect micro-openings or luminous areas with the naked eye (in a switched off state) and the contrast seems higher. The extension is preferably a maximum expansion of a micro-opening or of a luminous area parallel to the display area. Especially preferably the extension is less than or equal to the wavelength of the visible light and/or of the light to be passed through. It is e.g. at the most 2 μm, preferably at the most 1 μm or at the most 0.5 μm. As a result, in particular on the basis of the Rayleigh criterion, the exit angle of the light emerging from the luminous area becomes greater (and therefore advantageous, since one can view the display device from greater angles).

A micro-opening in this description is preferably also a subregion in e.g. the upper layer, which allows light to exit or pass through. Ideally a micro-opening is part of a micro-passage or arranged at the beginning or the end of the micro-passage.

In addition, it is advantageous, if the display comprises at least a VCSEL or at least an OLED or at least an LED or a micro display. This permits a simple realization of light information to be displayed by means of light-emitting luminous areas. Also it is advantageous, if light-emitting luminous areas are realized in the form of a display chip, preferably of an LED display, and/or of an OLED display and/or of a plasma display and/or of an FED display and/or of an SED display and/or of a LCD displays and/or of a laser and/or of a VCSEL display. Of course it is also possible that the light-emitting luminous areas do not form entire displays, but instead form single or several display chips, micro displays, LEDs, OLEDs, LCDs, laser and/or VCSEL, in particular in combination with a quantum dot.

Preferably the at least one VCSEL is inserted at least partially within a micro-passage. In this way the light generated from a VCSEL can ideally completely exit from a micro-opening on the surface facing a viewer. Because the generated light exits the display device almost completely, losses can be reduced, as a result of which the energy intake is also reduced. Furthermore the arrangement or at least partial insertion of at least one VCSEL in a micro-passage of the upper layer allows a reduction of the design height of the entire display device.

As already indicated, it is advantageous, if a light-emitting luminous area for example has one or more VCSELs or VCSEL lasers with e.g. 5 μm beam diameter, which are arranged on a substrate (such as for example on a Si wafer) as an array or in a matrix, e.g. in the form of a square with e.g. 50 μm edge length. the VCSEL lasers or VCSELs in a square preferably have emissions wavelengths differing from one another or, if they have the same emissions wavelength, are converted to different emissions wavelengths by wavelength devices (such as e.g. color-phosphorus elements or quantum dots). Many such units then form pixels or subpixels of the light-emitting luminous areas of the display device.

In addition, it is advantageous if the at least one OLED or the at least one LED or the micro display are arranged outside of a micro-passage. In this way it is possible that the at least one OLED or the at least one LED or the micro display is arranged for example underneath the upper layer, so that e.g. several OLEDs, LEDs or several light-generating pixels of a micro display can generate light for a micro-passage.

Furthermore, it is favorable if the upper layer is fabricated by means of a generative production process or if a fabrication of the upper layer is effected by means of a generative production process.

In doing so, advantageously this process is selective laser melting (SLM), selective laser sintering (SLS), selective head sintering (SHS), binder jetting, electron beam melting (EBM), fused deposition modeling (FDM), laminated object modeling (LOM), cladding, wax deposition modeling (WDM), contour crafting, cold gas dynamic spraying, stereo lithography (SLA), digital light processing (DLP) and/or liquid composite molding (LCM).

Preferably a fabrication of the upper layer comprises a forming of at least one layer and/or a forming of at least one functional layer and/or a forming of at least one beam shaping device. In the process the at least one beam shaping device can form a micro-passage. It is also possible to generate a micro-passage by means of a laser and/or by means of machining, preferably by means of milling and/or boring, and/or by means of a chemical process, preferably by means of etching, and/or by means of polishing and/or grinding. Also, during fabrication a carrier can be built, which makes possible the forming and/or fabrication of further structures, layers and/or beam shaping devices in simple manner.

Furthermore, it is possible that a plurality of beam shaping devices is arranged in a matrix. Hence the plurality of beam shaping devices functions as pixels or picture elements, which in total can compose an image.

In the process, it is advantageous if the upper layer is fabricated by means of a generative production process and comprises at least one beam shaping device, which forms a micro-passage. Hence, light can pass through the at least one beam shaping device and also through the upper layer.

Preferably a solar layer for generating power is created as at least one functional layer. This allows an embodiment of the display device without energy storage or with a relatively small energy storage, which can also be charged by the solar layer.

Furthermore, it is preferred that a touch-sensitive layer for acquiring input is created as at least one functional layer. In this way input of a viewer or user can be acquired via the display device, as a result of which the display device can be used as an input device e.g. for smartphones, smartwatches or tablets.

Preferably a pressure-sensitive layer for recording pressure is created as at least one functional layer. This embodiment also allows the input of a viewer or user to be acquired via the display device. As a result, the display device can also be used as an input device e.g. for smartphones, smartwatches or tablets. Furthermore, with the help of a pressure-sensitive layer for example the pulse of a smartwatch wearer can be determined.

Ideally, a temperature-sensitive layer for measuring a temperature is created as at least one functional layer. This allows the display device to record the external temperature and/or e.g. the temperature of the wearer of a smartwatch.

Furthermore provision can be made that a capacitive layer for measuring a capacity is created as at least one functional layer. Hence, the input of a viewer or user can be acquired via such a layer of the display device, as a result of which the display device can be used as an input device e.g. for smartphones, smartwatches or tablets.

In addition, it is favorable if when creating the at least one functional layer at least one sensing element is introduced into the functional layer. In this way for example a sensor chip can be introduced into a functional layer of the surface layer, in order to design this layer to record e.g. a temperature.

It is also advantageous if the at least one sensing element is configured as a touch sensor and/or as a temperature sensor and/or as a pressure sensor and/or as a capacitive sensor. In this way it is possible for the display device to acquire the input of a viewer or user, as a result of which the display device can be used e.g. for smartphones, smartwatches or tablets. The external temperature and/or e.g. the temperature of the wearer of a smartwatch can also be acquired.

Ideally a fabrication of the upper layer comprises a forming of a surface layer forming a surface or an outer surface, which forms the surface facing a viewer. The surface layer forming the surface or the outer surface ideally forms the region of the surface facing a viewer, which is physically tangible by the viewer. That is to say that this region or this surface layer or the surface comes into contact with the fingers, hand and hence the skin of a viewer. Accordingly quality features or a specified surface roughness can be placed on the surface layer, which makes the surface feel of a display device seem pleasant.

In a further advantageous embodiment the forming of the surface layer comprises an introduction of a precious metal into the surface layer or into the outer surface for finishing. In this way for example inert materials can be introduced into the surface facing a viewer. In this context, an inert material advantageously means material such as e.g. gold or silver, which, under the respective prevailing conditions do not react with potential reactants (for example air, water, reagents and products of a reaction) or react only to a minute extent.

Preferably the surface layer also forms a protection for the upper layer and/or increases the resilience of the upper layer and/or constitutes an embellishment for the upper layer, for example by means of a translucent plastic. Hence an appealing exterior can be combined with functional properties.

Ideally the forming of the surface layer or of the outer surface comprises an application of a surface structure. In this way the surface feel of the display device can be improved, in particular properties such as a lipophobic surface structure similar to the lotus effect can also be realized.

Preferably the surface structure is configured to be hydrophobic and/or oleophobic and/or bacteriophobic and/or translucent. In this way the surface layer or the upper layer of the display device or the outer surface can be configured to be repellent to water, oil and/or bacteria. Furthermore the translucent configuration allows light from the display device or its light-emitting luminous area or of the upper layer to pass through. Of course the surface structure can also be configured such that that incident light from the surface structure on the display device or the upper layer is also allowed to pass through. Preferably in the forming of the at least one beam shaping device the at least one beam shaping device is created at least partially within the upper layer. Hence the at least one beam shaping device can also be arranged within, outside of or at least partially within and partially outside. Each arrangement has different advantages to offer. Thus e.g. an arrangement of the at least one beam shaping device within the upper layer is useful if the upper layer of the display device is applied to an OLED. In this way the upper layer and the OLED can be manufactured separately from each other. For example an arrangement of the at least one beam shaping device outside of the upper layer is desirable if the upper layer of the display device is combined with a VCSEL. With this embodiment the space requirements can be reduced and a very thin display device can be realized.

Preferably the at least one beam shaping device forms a micro-passage. Preferably a micro-passage is understood as a connection of two sides of a layer, in particular of the upper layer. In other words, it is advantageous if at least one beam shaping device forming a micro-passage is configured similar to a borehole through a sheet metal plate. Thus a micro-passage or at least a beam shaping device can be a hollow space within a layer, in particular of the upper layer. The shape of the hollow space of the micro-passage/beam shaping device can in the process be any desired design, however a cylindrical shape is preferable. In other words, it can be advantageous to configure the at least one beam shaping device as a hollow space in a layer, wherein the hollow space is configured similar to a borehole or similar to a through hole, wherein the hollow space can be filled with a gas, in particular air.

In addition, it is favorable if the at least one beam shaping device is made at least partially of a translucent and/or electrically conductive material, in particular plastic. An at least partially translucent material allows e.g. the transmission or passing through of light, that is generated for example by an OLED or LED, through the upper layer, wherein preferably the loss of luminous power is minimized. Also, the at least partially translucent material can be a glass fiber, in particular made of a "Photonic Crystal Fiber" (PCF) or also "Photonic Bandgap Fiber" (PBG-Fiber). This glass fiber/this material conducts light nearly loss-free, wherein its properties can be adjusted virtually as required. By means of an electrically conductive material further properties of the display device can be improved, in particular the ability to record touch input or touch-sensitive input with high precision.

It is also favorable, if the at least one beam shaping device at least on its surface facing a viewer or side comprises an electrically conductive material and/or a non-transparent and/or a non-reflecting material. Ideally, by means of the at least one beam shaping device, which, at least on its surface facing a viewer comprises an electrically conductive material, the surface and/or the intermediate space between at least two beam shaping devices can be adjusted to improve the reception of radio signals for antennas. The electrically conductive material can be used for the reception of radio signals and for the transmission of such signals.

Furthermore, it is preferred that the at least one beam shaping device has a diffusion element, in particular a diffuser, and/or a collimator and/or a concentrator. In other words, preferably the at least one beam shaping device is configured or manufactured with a diffusion element, in particular a diffuser and/or a collimator and/or a concentrator. In the process a diffusion element or a diffuser can emit or diffuse light in a specified angular range. As a result the visual angle, at which light information is perceptible for a viewer, can be set. In addition with a collimator a parallel beam course can be generated, as a result of which light from a light-emitting luminous area, such as e.g. an LED or OLED, can be emitted or directed in a predefined direction in high concentrations. With the help of the concentrator it is possible, to concentrate light generated or emitted from a light-emitting luminous area, in particular from an LED, OLED or the like. As a result, the light output can be increased and hence for one thing the luminosity and also the light intensity can be increased, and for another thing energy can be conserved, so that a display device with a concentrator has a high energy efficiency.

Also, provision can be made that the at least one beam shaping device comprises an inlet and an outlet for light. In this way light can go from the inlet to the outlet.

Preferably, the inlet is arranged on at least one light-emitting luminous area of the display, wherein favorably the outlet is arranged on the surface of the upper layer facing a viewer. Hence the light of a light-emitting luminous area at the inlet of the at least one beam shaping device can also be introduced into it, and this light introduced at the outlet can be emitted again. In the preferred embodiment of the at least one beam shaping device with a diffuser and/or a collimator and/or a concentrator it is advantageous if the concentrator is arranged at the inlet, in order to introduce a maximum amount of light of a light-generating luminous area into the at least one beam shaped device. Advantageously the outlet of the at least one beam shaping device is or can be arranged within and/or on the micro-opening.

In addition, it is preferable if a diffusion element, in particular a diffuser, and/or a color filter element and/or a color converting element and/or a color-phosphorous element, in particular a quantum dot, is positioned at the outlet of the at least one beam shaping device. The diffuser allows an emission of the light from the at least one beam shaping device in a predeterminable angular range. In this way the visual angle can be adjusted to the respective requirements for a display device. For example a narrow visual angle can be suitable for display devices with sensitive data, while a large visual angle is advantageous for e.g. a smart watch. The color filter element, the color converting element and/or the color-phosphorous element, in particular in an embodiment as a quantum dot, can be used to convert the light of a specified wavelength and hence of a specified color into light of another wavelength or color. This is advantageous when using at least one VCSEL in the display device. Hence a display device can also be created with at least one VCSEL, said display device realizing the various colors in the RGB color space.

It is also advantageous if the outlet of the at least one beam shaping device is configured to acquire and/or evaluate light for a color and/or radiation measurement. In this way not only can light be emitted from the outlet, but rather also received from the inlet. Hence for example light information or electromagnetic radiation information can be conducted from the at least one beam shaping device, in particular its outlet, to the inlet. In this context it is preferable if not only a light-emitting luminous area, but rather also a light-sensitive sensor is arranged at the inlet. Said light-sensitive sensor can receive the light information or electromagnetic radiation information that has been received from the outlet and conducted to the inlet of the at least one beam shaping device and for example convert it into an electrical signal. In this way it is for example possible, to take a photo of the surroundings with the help of such a display device or to use the display device to copy a document. In particular in the acquisition and/or evaluation of light for a color measurement it is favorable if the mentioned sensor is configured to be sensitive for the corresponding light spectrum. In connection with the radiation measurement it is advantageous that not only visible light, but rather also radiation, in particular UV-radiation or also IR-radiation, is conducted from the outlet of the at least one beam shaping device to the inlet, in particular to the light emitting luminous area or a sensor arranged there which is sensitive to the mentioned types of radiation.

It is also favorable if the at least one beam shaping device is adapted to conduct light information in both directions, in particular light from the inlet to the outlet and from the outlet to the inlet of the at least one beam shaping device. Hence not only can light be emitted from the outlet, but rather also received from the inlet. As a result, for example light information can be conducted from the at least one beam shaping device, in particular its outlet, to the inlet. In this context it is preferable if at the inlet not only a light-emitting luminous area, but rather also a light-sensitive sensor is arranged. Said sensor can receive the light information, that has been received from the outlet and conducted to the inlet of the at least one beam shaping device, and for example convert it into an electrical signal. In this way it is for example possible to take a photo of the surroundings with the help of such a display device or to use the display device to copy a document. In particular in the acquisition and/or evaluation of light for a color measurement it is favorable if the mentioned sensor is configured to be sensitive for the corresponding light spectrum. In connection with the radiation measurement it is advantageous that not only visible light, but rather also radiation, in particular UV-radiation or also IR-radiation, is conducted from the outlet of the at least one beam shaping device to the inlet, in particular to the light emitting luminous area or a sensor arranged there which is sensitive to the mentioned types of radiation.

In addition, it is preferred that the at least one beam shaping device comprises a sacrificial element on the outlet side. In other words, it is advantageous if in one step of the method a sacrificial element is arranged at the outlet of the at least one beam shaping device. Said sacrificial element is preferably configured to be cylindrical, rectangular or conical and preferably translucent. Furthermore, it is advantageous if the sacrificial element receives and transfers light. The sacrificial element preferably serves, as the name says, as an element that can be sacrificed. In so doing the sacrificial element can, in particular in connection with a subsequent processing step, be removed, in order to form a substantially plane surface-forming surface layer or a substantially plane outer surface, for example by means of an abrading procedure, such as for example grinding or polishing. Thus with the help of the sacrificial element damage to the further beam shaping device is prevented, since the sacrificial element can be sacrificed without problems to create a substantially plane surface, without affecting the function of the at least one beam shaping device by its potential damage. Furthermore an abrading procedure can also be a processing by means of a laser and/or by means of machining, preferably by means of milling and/or boring, and/or by means of a chemical process, preferably by means of etching, and/or by means of polishing, to generate a surface layer.

A surface layer or a surface, that is designed "substantially plane", in the present description is preferably understood as a flatness tolerance. Described in other words, preferably an "substantially plane" surface layer or surface is a surface between two ideal planes at a distance of 0.5 millimeters.

Also, provision can be made that in forming of the at least one beam shaping device at least one sensing element is arranged between at least two beam shaping devices. Hence the space between two beam shaping devices can be used for sensory tasks.

Furthermore, it is favorable if the display, preferably its light-emitting side, has at least one sensing element. It is also possible that at least one sensing element is applied between the display and the upper layer. In this way it is also possible that the sensory element is arranged at different positions of the display device. This has advantages, in particular in connection with the respective manufacturing methods. Also, in this way ideal use can be made of the space between at least two beam shaping devices.

Furthermore, it is preferred that at least one sensing element is installed between the or within the light-emitting luminous areas of the display. In this way the display can be fabricated together with sensory elements, as a result of which the manufacturing of the display device is simplified. With the help of one or several sensory elements the display can e.g. detect the color of incident light or measure the ambient brightness, in order for example to adjust the level of illumination of the display.

Preferably the at least one sensing element has a sensor, in particular a two-dimensional and/or three-dimensional sensor, preferably an image sensor and/or a brightness-sensitive and/or a touch-sensitive and/or a pressure-sensitive and/or a gas-sensitive and/or a temperature-sensitive sensor, in particular a piezo element.

In this context it is for example preferable that the at least one sensing element is created or also arranged as a touch-sensitive sensor for acquiring input. In this way the input of a viewer or user can be acquired via the display device, as a result of which the display device can be used as an input device e.g. for smartphones, smartwatches or tablets. Furthermore, it is favorable if the at least one sensing element is created or also arranged as a pressure-sensitive sensor for recording pressure. This embodiment also allows the input of a viewer or user to be acquired via the display device. As a result, the display device can also be used as an input device e.g. for smartphones, smartwatches or tablets. Furthermore with the help of a pressure-sensitive sensor for example the pulse of a smartwatch wearer can be determined. Furthermore, it is possible that the at least one sensing element is created or also arranged as a temperature-sensitive sensor for measuring a temperature. This allows the display device favorably to record the external temperature and/or e.g. the temperature of the wearer of a smartwatch. Also, provision can be made that the at least one sensing element is created or also arranged as a capacitive sensor for measuring a capacity. Hence for example the input of a viewer or user can be recorded via such a sensor of the display device, as a result of which the display device can be used as an input device e.g. for smartphones, smartwatches or tablets. It is also advantageous if the at least one sensing element is configured as a touch sensor and/or as a temperature sensor and/or as a pressure sensor and/or as a capacitive sensor. In this way it is possible for the display device, to acquire the input of a viewer or user, as a result of which the display device can be used e.g. for smartphones, smartwatches or tablets. The external temperature and/or e.g. the temperature of the wearer of a smartwatch can also be acquired. One concrete embodiment of a touch-sensitive sensor is for example a piezo element or alternatively a pressure-resistive configuration of the display device. A temperature-sensitive sensor can for example be an electrical or electronic component, which supplies an electrical signal as a measure for the temperature. In so doing it can for example be components that change their resistance. The following elements are able to do this and are listed by way of example: negative temperature coefficient (NTC) thermistors decrease their resistance with an increase in temperature, positive temperature coefficient (PTC) thermistors increase their resistance with an increase in temperature, silicon measuring resistors, ceramic PTC thermistors. It can also be components that directly supply a processable electrical signal. For example, this includes integrated semiconductor temperature sensors (Solid-state circuits), which supply a current proportional to their temperature or a voltage proportional to their temperature or a digital signal depending on their temperature. Of course it can also be a diode or a temperature sensor with oscillating quartz as a measuring element. Also conceivable are so-called thermo-elements, which use the Seebeck effect to convert a temperature difference into an electrical voltage. In addition pyroelectric materials can be used, for example as they are known from a pyrometer or thermal imaging cameras, wherein they operate without contact and measure the thermal radiation. Mechanical temperature switches, e.g. bimetal switches, which activate a switch by bending a bimetal, can also be used. A gas-sensitive sensor has the advantage that it can detect gases such as for example ozone, $CO_2$ etc. In the process, a temperature-sensitive sensor can be used to record a temperature, e.g. the ambient temperature and/or the temperature of the display device or of a specified component. With the help of a 2-dimensional and/or 3-dimensional embodiment of sensors it is also possible to arrange a sensor not only two-dimensionally within the upper layer of the display device, but rather also to configure it along the height or thickness of the upper layer. In this way considerable installation space can be saved, or also used for additional purposes. Hence highly functional units can be fabricated.

In addition, it is favorable that at least one functional layer and/or at least one layer of the upper layer and/or at least one beam shaping device is created by means of a thin layer method. In this way very thin layers and hence a very think or light display device can be manufactured.

Furthermore, it is advantageous if the formation by means of thin layer methods comprises a sputtering and/or a galvanic application and/or a nanoimprint and/or a roller embossing method and/or an injection molding method. With the help of the aforementioned methods structures in the micrometer and nanometer range are feasible. Hence it is also possible to structure and manufacture an upper layer in the mentioned ranges. Preferably the forming comprises a sputtering with a metal, in particular with aluminum or titanium or gold or silver. To a great extent the sputtering is used as a substep in sputter deposition, a fine-vacuum based coating technique belonging to the group of PVD methods. Here it is used to spray a material, which subsequently deposits on a substrate and forms a solid layer. In the area of coating technology sputter deposition is frequently just referred to as "sputtering". Galvanic application is preferably understood as electroplating or nickel electroplating or the electrochemical deposition of metallic deposits on substrates. Nickel electroplating is a galvanization technique in which a thin layer of nickel is applied to a metal object. The nickel can be decorative, offers corrosion resistance, resistance to wear, or can be used for the fabrication of worn or small parts. The term nanoimprint or nanoimprint lithography is preferably understood as a nanolithography method for the cost-effective manufacturing of nanostructures. In so doing by means of a nanostructured stamp, which forms a negative, a positive is "stamped". As a rule monomers or polymers are used for the positive, which are hardened after the embossing. In the roller embossing method the at least one beam shaping device is embossed for example by a roller made of a plastic material. This allows a simple, cost-effective and rapid manufacturing of beam shaping devices. The injection molding method is a primary shaping process, which is used as a rule in plastic processing. In so doing, the respective material is liquefied (plasticized) with an injection molding machine and injected under pressure into an injection molding tool forming the mold. In the tool the material transitions back to the solid state by cooling or a cross-linking reaction and is removed as a finished part after opening the tool. In the process the tool determines the shape and the surface structure of the finished part.

It is also advantageous if the forming comprises a chemical or physical vapor deposition or a sol-gel process.

A group of vacuum-based coating methods or thin film technologies is referred to as physical vapor deposition (PVD for short). Unlike chemical vapor deposition, with the help of the physical methods a base material is converted into the gas phase. The gaseous material is subsequently directed to the substrate to be coated, where it condenses and forms the target layer. The methods of physical vapor deposition include e.g. thermal evaporation, electron beam evaporation, pulsed laser deposition, cathodic arc deposition, molecular beam epitaxy, sputtering or ion plating. In the process, with the help of the mentioned methods of vapor deposition virtually all metals and also carbon can be deposited. In supplying reactive gases like oxygen, nitrogen or hydrocarbons, oxides, nitrides or carbides can also be deposited or manufactured. As a rule, physical vapor deposition is used to manufacture thin layers in the range of several nanometers to a few micrometers.

A group of coating methods for manufacturing microelectronic components and fiber-optic cable is referred to as chemical vapor deposition (CVD). In the process, a surface of a substrate is heated, as a result of which, due to a chemical reaction a solid component is deposited from the gas phase. The method of chemical vapor deposition is characterized by at least one reaction on the surface of the workpiece to be coated. At least one gaseous starting compound and at least two reaction products—of which at least one must be in the solid phase—must be involved in the reaction. One special feature of this method is the uniform layer deposition. In contrast to physical methods, chemical vapor deposition also makes possible the coating of complex three-dimensionally shaped surfaces.

Sol-gel process refers to a method for producing non-metallic inorganic or hybrid polymer materials from colloidal dispersions, the so-called sols or solutions. The smallest particles are generated from base materials in solution in initial basic reactions. By means of a special further processing, powders, fibers, layers or even aerogels can be generated.

In addition, it is preferred that the forming of the at least one functional layer and/or of the at least one layer of the upper layer and/or of the at least one beam shaping device comprises a molding of a material. In contrast to injection molding, in molding the material is preferably not injected into a mold under pressure, but rather—similar to the molding procedure for large components for e.g. engines—a casting compound is poured into a mold or for example cast on one layer. In this way is a substantially plane surface layer forming a surface or a plane outer surface can be produced easily and cost-effectively.

Furthermore, it is preferred that the cast material is hardened by means of UV light, applied heat or dissipated heat. This allows the casting compound to flow first into the cavities of the mold and hence prevent air pockets by means of a time delay after the casting of the material. It is also possible prior to the hardening by means of light or heat to expose the cast or molded compound to vibrations, which can move the air pockets outward. In this way—as already indicated—air pockets can be prevented and a high quality layer can be produced.

Ideally the forming of the at least one functional layer and/or of the at least one layer of the upper layer and/or of the at least one beam shaping device comprises an application by means of a spackling process. In such a process—expressed in simplified terms—a spackling compound is applied by means of a trowel, in order to form an upper layer or a part of the upper layer, in particular the surface layer forming the surface or the outer surface. The advantage of this process lies in the easy application and distribution of a spackling compound.

In the spackling process it is ideal if a spackling compound penetrates into the micro-openings, and preferably at least partially into the micro-passages, in order to form at least one beam shaping device, in particular a diffuser. In this way the spackling compound can not only form a part of the upper layer, in particular the surface layer forming the surface or the outer surface, but rather also simultaneously at least one beam shaping device, advantageously in embodiment as a diffuser.

Preferably the spackling compound comprises a semiconductor material forming a quantum dot. Hence with the help of the spackling compound not only can a diffuser be generated, but rather also a quantum dot, with whose help for example the generated color or the generated monochromatic light of a VCSEL can be changed to any color is, as a result of which e.g. a pixel is created in the RGB space.

Furthermore, it is preferred that the forming of the at least one functional layer and/or of the at least one layer of the upper layer and/or of the at least one beam shaping device comprises a fusion. In this way a material can be converted e.g. by means of heat application from a powdery form to a solid, fused form. This manufacture favorably allows the production of a plane surface on a layer.

It is also favorable if the forming of the at least one functional layer and/or of the at least one layer of the upper layer and/or of the at least one beam shaping device comprises a generative production method, in particular stereo lithography (SLA). In so doing can it can preferably also be a selective laser melting (SLM) selective laser sintering (SLS), selective head sintering (SHS), binder jetting, electron beam melting (EBM), fused deposition modeling (FDM), laminated object modeling (LOM), cladding, wax deposition modeling (WDM), contour crafting, cold gas dynamic spraying, stereo lithography (SLA), digital light processing (DLP) and/or liquid composite molding (LCM). Frequently rapid prototyping methods for rapid and cost-effective production of models, patterns, prototypes, tools and end products are referred to as generative production methods or as additive production. As a rule, with such production an object is produced directly on the basis of data models from shapeless fluids, powders etc. or neutrally shaped strip-shaped or wire-shaped material by means of chemical and/or physical processes.

Provision can also be made that the forming of the at least one functional layer and/or of the at least one layer of the upper layer and/or of the at least one beam shaping device comprises a reworking of the upper layer. The reworking of the upper layer can for example be manufacturing a specified surface structure. In particular the forming comprises a reworking of the upper layer by means of a laser and/or by means of machining, preferably by means of milling and/or boring and/or by means of a chemical process, preferably by means of etching, and/or by means of polishing, to produce a surface layer or an external surface. With the help of the aforementioned methods it is for one thing possible, to create a substantially plane surface or a substantially plane surface layer of the upper layer that is facing a viewer. For another thing, a passage or a micro-passage can also be placed in the upper layer. This happens for example by means of milling and/or boring and/or etching a passage through the upper layer. In this way for example a passage for light can also be created, with the help of which it is for example possible, to conduct or let light from a light-generating luminous area from one side of the upper layer to the other.

In addition, it is possible that the reworking also comprises a removal of a carrier and/or of a carrier layer, upon which various structures, layers and/or beam shaping devices can be easily fabricated or created. It is also conceivable that the carrier layer can be omitted. This is ideally the case e.g. if the upper layer is not or is not arranged on the carrier layer or on a carrier, but rather on the display of the display device or a glass of the display.

In addition, it is advantageous if the fabrication of the upper layer comprises a generative production method, in particular a molding of a material. In the molding the material is preferably not injected into a mold under pressure, but rather—similar to the molding procedure for large components for e.g. engines—a casting compound is poured into a mold or for example cast on one layer. In this way a substantially plane surface layer forming a surface of the upper layer or a plane external surface can be produced simply and cost-effectively. Furthermore, it is preferred if here too the cast material is hardened by means of UV light, applied heat or dissipated heat. This allows the casting compound to flow first into the cavities of the mold and hence prevent air pockets by means of a time delay after the casting of the material. It is also possible prior to the hardening by means of light or heat to expose the cast or molded compound to vibrations, which can move the air pockets outward. In this way—as already indicated—air pockets can be prevented and a high quality layer can be produced.

It is also preferred that the fabrication of the upper layer comprises a filling of the intermediate space between at least two beam shaping devices. This approach for example makes it possible to first manufacture beam shaping devices, position them correctly to one another, and subsequent to this to join the individual beam shaping devices separated from one another by means of filling the intermediate spaces between the beam shaping devices. Hence not only can beam shaping devices or at least one beam shaping device be manufactured prior to the fabrication of the upper layer, but rather also undergo a quality control, wherein Scrap can be avoided in the production of a display device.

Furthermore, it is favorable if the quantity of material used for filling, in particular plastic, advantageously opaque plastic, or metal, covers the at least one beam shaping device, at least partially, preferably completely. The covering of the at least one beam shaping device serves the purpose, in a subsequent manufacturing step, in particular in the case of a reworking of the upper layer, of applying material, which also facilitates a reworking.

Provision can also be made that the quantity of material used for filling, in particular plastic or metal, covers the at least one beam shaping device at least on the surface facing the viewer such that at least a region or a subregion of the sacrificial element is enclosed by material. In other words, it is advantageous if the sacrificial element is covered by the material used for filling such that preferably in the case of a reworking of the created upper layer or of the surface layer forming the surface or of the surface facing the viewer the sacrificial element is removed, at the most completely, preferably by 95%. The removal can for example be realized by means of milling and/or etching and/or polishing.

Furthermore, it is favorable if a substantially plane surface facing the viewer is created on the upper layer. In other words, it is advantageous if a surface layer of the upper layer forming a surface has a substantially plane surface facing the viewer. In the forming of such a plane surface not only is a uniform exterior of the display device produced, but rather also a feel which gives a user or a viewer the subjective impression that the display device has been fabricated of a single material and hence in one piece. In addition, it is advantageous to create a substantially plane surface, since further layers and/or surface structures can be applied to this which perform various functions. Thus, it is for example possible to apply a surface structure that is configured to be hydrophobic and/or oleophobic and/or bacteriophobic and/or translucent.

Preferably, in the forming of the substantially plane surface an optical passage is created, so that light from the at least one beam shaping device can enter and/or exit. The forming of a passage can for example be realized by means of boring and/or etching and/or milling. Of course other material removing methods for manufacturing a passage are conceivable.

In addition, it is favorable if the forming of the substantially plane surface comprises a processing of the surface facing the viewer of the display device by means of a material removing method, in particular by means of grinding and/or polishing, and/or by means of a laser and/or by means of machining, in order to produce a substantially plane surface layer or a substantially plane external surface. In other words, it is favorable if a substantially plane surface layer of the upper layer forming a surface or a substantially plane external surface is produced with the help of the mentioned methods. In the forming of such a plane surface or surface layer not only is a uniform exterior of the display device produced, but rather also a feel which gives a user or a viewer the subjective impression that the display device has been fabricated of a single material and hence in one piece. This imparts an especially high quality degree of processing. It is also possible with the help of such a display device, to design it to be water resistant on the sides of the surface layer or of the upper layer. In addition, it is advantageous to create a substantially plane surface, since further layers and/or surface structures can be applied to this which perform various functions. Thus, it is for example possible to apply a surface structure that is configured to be hydrophobic and/or oleophobic and/or bacteriophobic and/or translucent.

Provision can be made that the processing of the surface facing the viewer comprises a generation of a common plane surface, wherein preferably the upper layer and a plurality of beam shaping devices, in particular their outlets and/or their sacrificial elements can be processed such that light can exit from the outlets and/or sacrificial elements of the plurality of beam shaping devices. In connection with the aforementioned features it is advantageous the surface facing the viewer is processed such that the outlets of the plurality of beam shaping devices allow light to exit. In this way light from one side of the upper layer goes to the other side or preferably from the inlet to the outlet and favorably also from the outlet to the inlet.

Furthermore, it is favorable that the ratio of the area of the inlet of the at least one beam shaping device and/or of the maximum area of the beam shaping device to the area of the outlet of the at least one beam shaping device is less than or less than or equal to 1:25. This ratio allows a maximum light output or a maximum amount of light to be conducted from the inlet to the outlet of the at least one beam shaping device. Hence losses can also be reduced to a minimum.

It is also advantageous if the ratio of the area the at least one beam shaping device exiting through the upper layer to the area of the upper layer is less than or less than or equal to 1:10, in particular between 1:100 to 1:94. With the help of this ratio display devices can be created, that offer an optimum resolution with an optimum utilization of the space made available by a display device for light emitting luminous areas or for beam shaping devices.

Preferably the distance from inlet to outlet of the at least one beam shaping device in proportion to the maximum diameter or diagonal at the inlet of the at least one beam shaping device is equal to or less than 10:1, in particular equal to or less than 1:1. This embodiment also makes it possible to minimize losses and emit a maximum of light or light intensity or amount of light at the outlet of the at least one beam shaping device in the direction of a viewer.

Ideally, an outlet of the at least one beam shaping device has a diameter or a diagonal less than 1 mm, preferably less than 50 µm, in particular less than 30 µm, preferably less than 20 µm, especially preferably less than 8 µm. The larger the diagonal the easier a manufacturing is, in particular for large-area display devices, for example such as large-area displays for advertising at airports or train stations. The smaller the diagonal the better the resolution for small-area display devices, for example such as mobile phones and/or smartphones and/or tablets.

Provision can also be made thon the surface and/or the intermediate space between at least two beam shaping devices is adapted to suppress light reflections and/or to absorb light for a higher contrast and/or to improve the reception of radio signals for antennas. By suppressing light reflections for example the contrast can be increased, as a result of which a viewer gets the impression of a deeper shade of black. The same holds true if light is absorbed. Ideally by means of the at least one beam shaping device, which, at least on its surface facing a viewer comprises an electrically conductive material, the surface and/or the intermediate space between at least two beam shaping devices can be adjusted to improve the reception of radio signals for antennas. The electrically conductive material can be used for the reception of radio signals and for the transmission of such signals.

Preferably the surface and/or the intermediate space between at least two beam shaping devices is adapted to measure the composition of air and/or gas and/or radioactivity. In other words, it is advantageous if the surface and/or the intermediate space between at least two beam shaping devices has sensors with which the air and/or gas and/or radioactivity can be measured or recorded. In this way a display device can be used not only to display information, but rather also to record environmental conditions.

Furthermore, it is favorable if the surface and/or the intermediate space between at least two beam shaping devices is adapted to measure noises and/or emit noises and/or to detect odors. With the help of this embodiment a display device can also detect environmental conditions. Furthermore, with the help of the emission of noises e.g. warning signals and/or a speaker phone and/or a ringing, triggered by a caller, can be generated.

Preferably the surface and/or the intermediate space between at least two beam shaping devices is adapted to comprise actuators, in particular micromotors, send and receive antennas, movable microparts, micro-melt elements, micro-electromagnetic or magnetic elements, micro-air compression or micro-hydraulic elements, preferably having a shape memory material. With the help of the actively movable elements, such as e.g. motors, shape memory material or actuators, a display device can be created whose shape can be changed by means of the application of an energy, or current/voltage. Hence such a display device can e.g. be brought from a plane configuration to a curved configuration with predefinable curvature.

In conclusion, it can be reported that with the help of the specified features a display device can be created whose design, thickness and mechanical stability far exceed the previous prior art.

In the process the complete display device or the display device itself can ensure an increased mechanical stability and can have a smaller diameter or overall depth compared to conventional display devices.

Among other things, one critical advantage of the inventive display device is that it is superior to conventional, known display devices, regardless of type (in particular LCD or OLED or Plasma or FED). First and foremost, this is because conventional display devices have to have a transparent protective layer, usually made of reinforced glass or plastic, such as sapphire glass, so-called "Gorilla" glass or bullet-proof glass etc. with a thickness of 0.5 mm to 1.5 mm. This transparent protective layer, which the present invention can omit, contributes considerably to the weight of the entire display device. Hence, as a logical consequence, the inventive display device is lighter than conventional display devices.

Furthermore, it is part of this invention that with the help of the manufacturing methods presented here, special and unique design effects and a high mechanical stability of a display device can be achieved. In particular when switched off or in the parts of this innovative display device that are not illuminated, iridescent color effects as with butterflies can arise or be generated. All in all, the inventive manufacturing method for a display device is a method that offers unique design effects, possibilities and features for a display device that are neither possible nor desirable in the case of conventional display devices.

A further preferred feature of this invention arises because a protective glass is no longer necessary. In conventional display devices protective glasses (or plastics) are relatively thick, so that they protect a display device mechanically. However, such a glass itself not very elastic or fragile. Therefore, as a rule protective glasses for display devices are at least 0.5 mm to 1.5 mm thick and sometimes quite expensive to manufacture. In case of breakage they are difficult and costly to replace.

Since according to the inventive manufacturing method a display device comprises substantially light-emitting luminous areas and an upper layer, there is no longer any need for a thick, transparent protective glass.

In the process, the material for filling or filling material can be formed of less fragile metal. Hence with the inventive manufacturing method at least four important features of an innovative display device can be achieved.

First, a display device manufactured according to the inventive method is far less fragile than conventional display devices. If e.g. a portable device with a conventional display device falls to the floor, in virtually all cases the display device breaks, because the protective glass is directly connected to this display device.

Secondly, with the help of the inventive manufacturing method a display device can be created, which is implemented considerably thinner in comparison to conventional display devices.

A conventional display device consists of several layers, which can be very thin, however the protective glass (or plastic) must remain relatively thick to ensure a protective function or to protect itself. This is not the case with a display device according to the inventive manufacturing method. The light-emitting luminous areas can be kept extremely thin (as with the best conventional display devices, e.g. 100 µm to 200 µm for OLED), wherein the thick protective glass of e.g. 700 µm can be replaced with only 100 µm to 300 µm filling material or metal (including beam shaping devices).

This example clearly shows that a conventional display device totaling e.g. 1 mm can be replaced by this display device according to the inventive manufacturing method with e.g. a total of 250 µm. This is a huge advantage for portable devices, such as e.g. a watch, in which case historically, manufacturers were always striving to design them extremely thin (and light).

In this respect this invention represents a special advantage for e.g. an OLED or an OLED display device. OLEDs additionally require a protective glass for protection from moisture and oxygen.

To ensure this protection, either the protective glass can be extremely thin (because with this invention it no longer has to provide mechanical protection) or the optics and/or protective material (e.g. metal) performs or replaces the protective function of the protective glass against moisture and oxygen directly in the manufacturing. Of course, this is not limited to OLED display devices, it can also be applied for liquid crystals (LCD), VCSEL or FED or plasma display devices directly during manufacturing or afterwards.

Thirdly, the display device according to the inventive method can be manufactured considerably lighter, since metals like aluminum, lithium or titanium can be similar or even lighter than glass, above all if they have only a fraction of the necessary thickness (or volume) of a conventional protective glass, with the same or much higher strength.

Fourthly, with the help of the inventive manufacturing method a display device can be created, that is significantly more flexible in comparison to conventional display devices. This flexibility results favorably from the advantage that brittle or fragile materials, such as e.g. glass, are not used or largely not used. Furthermore, by using an elastic, flexible material or filling material, which is applied in the intermediate spaces between the beam shaping devices, a bending of the entire display device can be facilitated. In this way the display device can, with the help of the elastic filling material, deform or bend in all directions. In the process, upon bending, the at least one beam shaping device can remain unchanged, as a result of which its optical properties are preserved. In other words, it is favorable if only the material between the beam shaping devices or the filling material is flexible or configured to be flexible.

Hence flexible displays or display devices can also be implemented.

The four points mentioned above are in particular advantageous for all portable devices, in particular in combination with a smaller reflective surface (when exposed to sunlight), and greater conservation of energy.

Reference is explicitly made to the fact that with the help of all of the aforementioned features not only a method for producing a display device, but rather also the display device itself can be configured. Hence the aforementioned features serve not only as features of the method, but rather also as features of the device, as a result of which also a display device can be configured.

Furthermore it is expressly pointed out that the features of the method for producing a display device, as mentioned above, can be used individually or combined with one another in the display device.

In other words, the features mentioned above under the method for producing a display device can also be combined with further features here under the display device.

Advantageously the display devices, in particular obtained by a method with the aforementioned features, comprise a display and an upper layer. In so doing the upper layer ideally serves the purpose of protecting the display, in particular from external influences which are triggered by falls.

In the process, ideally the upper layer is arranged at light-emitting luminous areas of the display and furthermore has a substantially plane surface facing a viewer. In this way, light of the luminous areas can get through the upper layer optimally, wherein a substantially plane surface facing a viewer constitutes a pleasant feel for a user of the display devices.

It is also advantageous if the upper layer comprises micro-passages for letting through generated light of the light-emitting luminous areas of the display, which form micro-openings in the surface facing a viewer. Hence it becomes possible for light generated from the luminous areas to pass through the upper layer.

In addition, it is preferred that the upper layer comprises at least one beam shaping device, which forms a micro-passage and comprises an inlet and an outlet for light. Preferably the upper layer has at least one beam shaping device, which comprises a sacrificial element on the outlet side. Advantageously the sacrificial element can be sacrificed to form a substantially plane surface, without affecting the function of the at least one beam shaping device.

It is also favorable if the at least one beam shaping device comprises at least partially a translucent material, in particular a glass fiber, and/or an electrically conductive material (8), in particular plastic, and preferably is embedded in the upper layer, which is fabricated by means of a generative production process.

In addition it is preferred that the at least one beam shaping device has a diffusion element, in particular a diffuser, and/or a collimator and/or a concentrator. Hence light can be concentrated, collimated and/or diffused with the help of the at least one beam shaping device.

In addition, it is favorable if the inlet is arranged on at least one light-emitting luminous area of the display. Advantageously the outlet is arranged on the surface of the upper layer facing a viewer. Hence the orientation of the at least one beam shaping device is determined with respect to the luminous area of the display or with respect to the display.

It is also possible that at the outlet of the at least one beam shaping device a diffusion element, in particular a diffuser and/or a color filter element and/or a color converting element and/or a color-phosphorous element, in particular a quantum dot is positioned. The diffuser allows an emission of the light from the at least one beam shaping device in a predeterminable angular range. In this way the visual angle to the respective requirements for a display device can be adjusted. So, for example a narrow visual angle can be suitable for display devices with sensitive data, while a large visual angle is advantageous for e.g. a smart watch. The color filter element, the color converting element and/or the color-phosphorous element, in particular in an embodiment as a quantum dot, can be used to convert the light of a specified wavelength and hence of a specified color into light of another wavelength or color. This is advantageous when using at least one VCSEL in the display device. Hence a display device can also be created with at least one VCSEL, said display device realizing the various colors in the RGB color space.

It is also advantageous if the upper layer comprises substantially metal and/or a non-transparent and/or a non-light reflecting plastic or material. Preferably the metal and/or the plastic is a robust material or a material that is able to resist external mechanical influences, for example such as falls and/or scratches and/or moisture.

It should also be noted that preferably forming can be understood as fabrication or ideally fabrication can also be understood as forming.

In the following the invention will be explained in greater detail on the basis of exemplary embodiments in combination with associated drawings. The figures show schematically:

In the subsequent description the same reference numerals will be used for the same objects.

Figure 1:
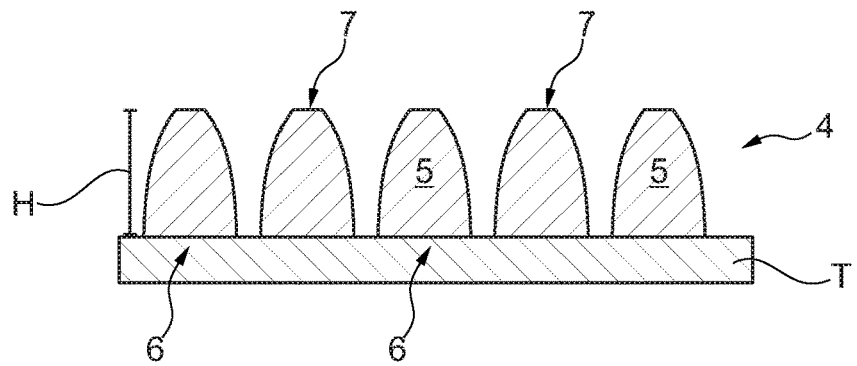
FIGS. 1 to 5 show a first exemplary embodiment of a manufacturing method of a thin and substantially fracture resistant display device in various individual steps.

It should be noted that the subsequent exemplary embodiments are to be understood as possible embodiment variants of a possible manufacturing method.

Due to the bandwidth of the subject matter or method defined in the claims, further embodiments are conceivable and possible.

FIGS. 1 to 6 show a first exemplary embodiment of a manufacturing method of a thin and substantially fracture resistant display device 1 in various individual steps.

In the mentioned figures—presented in summarized form—a method for producing a thin and substantially fracture resistant display device 1 with a display 2 is introduced. In so doing an upper layer 4 is arranged over light-emitting luminous areas 3 of the display 2, having a surface facing a viewer O. The upper layer 4 comprises substantially metal or a non-transparent or a non-light reflecting material.

In the upper layer 4 micro-passages are formed for allowing generated light of the light-emitting luminous area 3 of the display 2 to pass, said micro-passages forming micro-openings A in the surface facing a viewer O.

In a first portion of the inventive method comprising several steps, the upper layer 4 is fabricated.

This happens among other things in a first step—presented in FIG. 1—on a carrier T by means of laminated object modeling, a generative production method. In the process, in the fabrication of the upper layer 4—presented concretely—several beam shaping devices 5 are created, wherein they are created at least partially out of a translucent material, in particular plastic. These beam shaping devices 5 form within the upper layer 4 the micro-passages for allowing light to pass.

In the process in the present example according to FIG. 1 the beam shaping devices 5 can in each case have a diffusion element, in particular a diffuser (not shown in FIG. 1), and/or a collimator (not shown) and/or a concentrator. In FIG. 1 every beam shaping device 5 has furthermore a parabolic cross-section, as a result of which a concentrator is formed. This allows a concentration of incident light. In the process the lower end, which in comparison to the upper end is arranged on the carrier T, has a greater cross-section or diameter.

In so doing the lower end of every beam shaping device 5, which is arranged on the carrier T, forms an inlet 6 and the upper end forms an outlet 7 for light.

Figure 2:
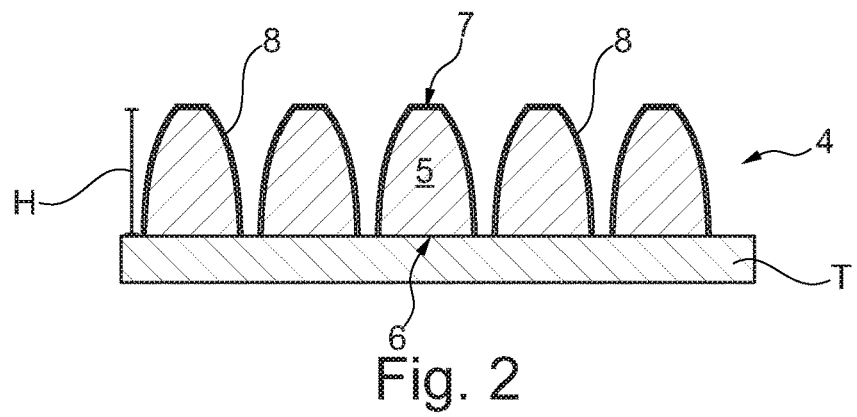

In a second manufacturing step—presented in FIG. 2—the surface of the beam shaping devices 5 is covered or coated or painted with an electrically conductive material 8. In other words, the beam shaping devices 5 now comprise, at least on their surface facing a viewer, an electrically conductive material 8. The material 8 can also be configured in addition without electrical conductivity or only opaquely.

In FIG. 2 in the process the beam shaping devices 5 are created by means of a thin layer method, which is sputtering and/or a galvanic application and/or a nanoimprint and/or a roller embossing method and/or an injection molding method. In the present case the forming of the beam shaping devices 5 comprises a sputtering with a metal, in particular with aluminum. As a result, in addition to the electrical conductivity, a light-reflecting surface can be generated easily and cost-effectively from a light material. Hence light within the concentrator of every beam shaping device 5 or within every beam shaping device 5 can be reflected on the areas covered by metal such that at the inlet 6 incident light is concentrated or bundled to the outlet 7 of every beam shaping device 5 by means of the concentrator.

Figure 3:
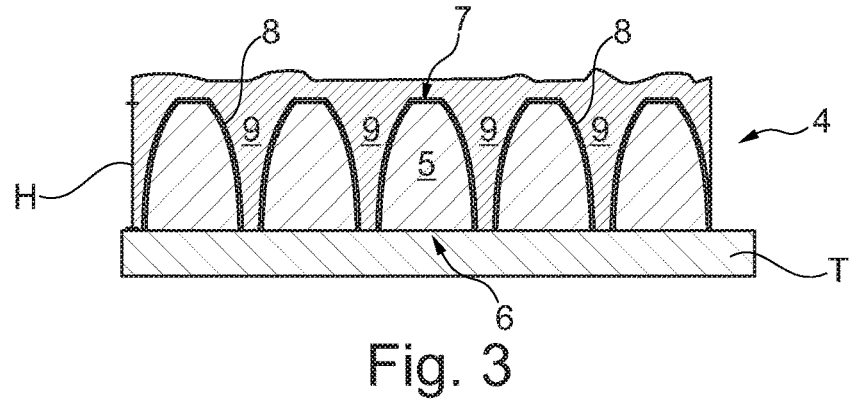

In FIG. 3 a further substep of the fabrication of the upper layer 4 is schematically shown. In so doing the fabrication of the upper layer comprises a generative production method, in particular a molding of a material. The molding or fabrication of the upper layer features a filling of the intermediate spaces 9 between the beam shaping devices 5. As a result among other things the mechanical stability is increased.

In addition, the quantity of material used for filling, which in the present case is preferably an opaque plastic or metal, completely covers the beam shaping devices 5. As shown, during molding no substantially plane surface can be created on the upper layer 4.

Figure 4:
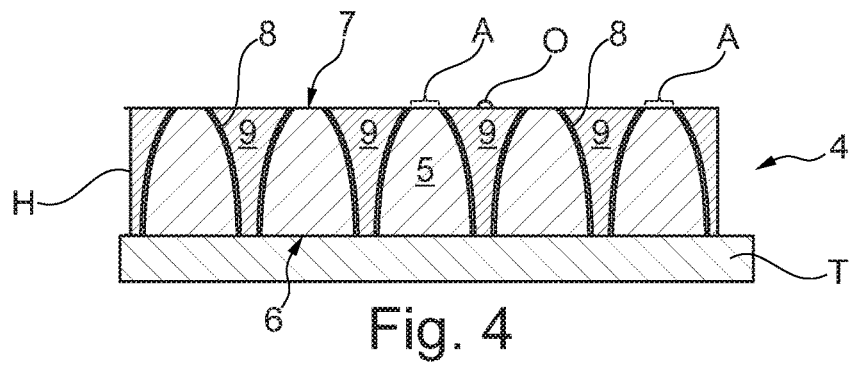

Therefore, in a subsequent step—presented in FIG. 4—a substantially plane surface facing the viewer O is created on the upper layer. In the process, in the forming of the substantially plane surface an optical passage is created, so that light from the beam shaping devices 5 can enter and/or exit. As a result the beam shaping devices 5 are created at least partially or completely within the upper layer.

To express the above described circumstances relating to FIG. 3 in other words, by creating of a plane surface O micro-openings A are generated in the upper layer 4, which make it possible for light at the outlet 7 of the beam shaping devices 5 to exit.

The forming of the substantially plane surface O comprises a processing of the surface facing the viewer O of the display device 1 by means of a material removing method, in particular by means of grinding and/or polishing. It is also possible by means of a laser and/or by means of machining, preferably by means of milling and/or boring, and/or by means of a chemical process, preferably by means of etching, and/or by means of polishing and/or grinding to generate a surface O or a surface layer.

To summarize for the step described in FIG. 4 it can be pointed out that the processing of the surface facing the viewer O comprises a generation of a common plane surface, wherein the upper layer 4 and a plurality of beam shaping devices 3, in particular their outlets 7, are processed such that light can exit from the outlets 7 of the beam shaping devices 3.

Generally speaking, the fabrication of the upper layer 4 happens by means of a generative production method, wherein along with the forming of the beam shaping devices 5, the fabrication of the upper layer 4 can also feature a forming of a further layer and/or at least one functional layer.

In so doing the fabrication of the upper layer comprises a forming of a surface layer forming a surface or an outer surface, which forms the surface O facing a viewer. In the present example however the upper layer 4 only has one layer, in which the beam shaping devices 5 are embedded. Hence in FIG. 4 the upper layer 4 corresponds to the surface layer.

Furthermore, the forming of the surface layer can comprise an application of a surface structure, which can be configured to be hydrophobic and/or oleophobic and/or bacteriophobic and/or translucent.

After the processing of the surface facing the viewer O by generating a common plane surface the carrier T is likewise removed. This happens with the help of an abrasive procedure, in particular by means of grinding and/or polishing. It is also possible to remove the carrier T by means of a laser and/or by means of machining, preferably by means of milling and/or boring, and/or by means of a chemical process, preferably by means of etching, and/or by means of polishing and/or grinding.

Figure 5:
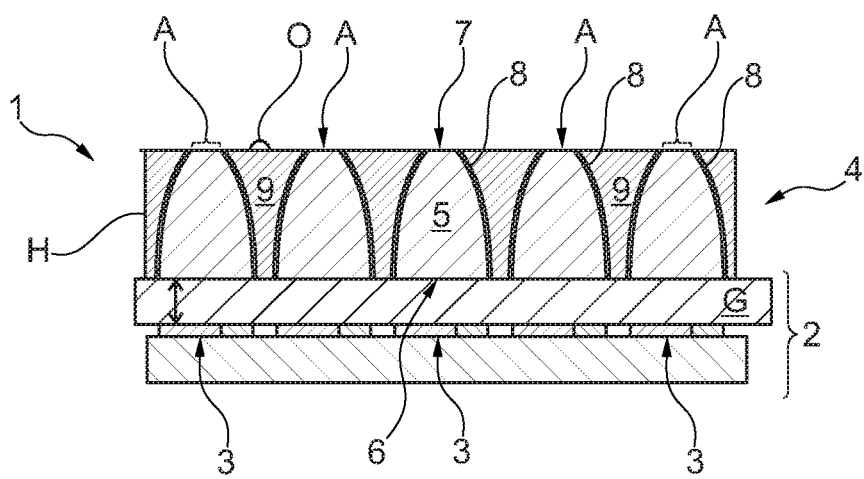

In a further step—presented in FIG. 5—the display 2 for forming of the thin and substantially fracture resistant display device 1 is arranged at the upper layer 4 from FIG. 4.

In so doing, the display comprises 2 OLEDs or a micro display as light-emitting luminous areas 3, which are protected by a glass substrate G. The upper layer 4 having a surface facing a viewer O is arranged on these light-emitting luminous areas 3 of the display 2 or on the glass substrate G.

More precisely, the micro-passages formed in the upper layer or the beam shaping devices 5 forming the micro-passages are arranged with their inlet 6 at light-emitting luminous areas 3 of the display 2 or on the glass substrate G. In the process, ideally each beam shaping device 5 is arranged above a light-emitting luminous area 3, so that a maximum degree of light of the beam shaping device can be made available.

As a result the outlets 7 of the beam shaping devices 5 are arranged on the surface facing a viewer O of the upper layer 4. Viewed from the other side, the OLEDs or the micro display 2 outside of the micro-passages, formed by the beam shaping devices 5 within the upper layer 4, are arranged such that the light generated from the luminous areas 3 can pass through the upper layer 4. In other words, light from the light-emitting luminous areas 3 enters into the inlets 6 and exits the outlets 7. Hence—as already indicated—the micro-passages or the beam shaping devices 5 forming the micro-passages are used to let through light, so that generated light of the light-emitting luminous areas of the display in the surface O facing a viewer can exit from the micro-openings A.

Figure 6A:
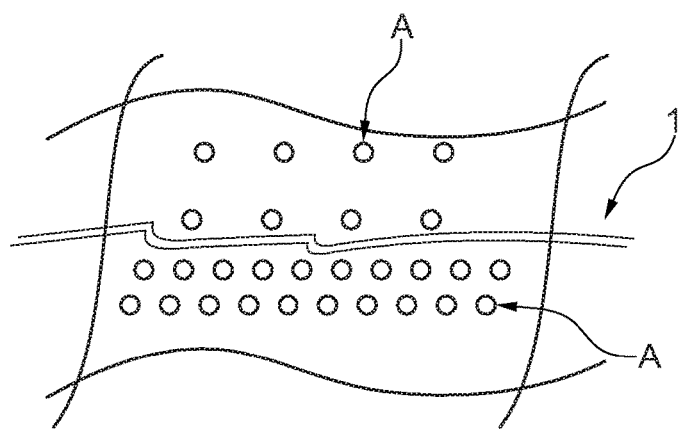
FIG. 6a shows a top view of a section of a created, inventive display device.

FIG. 6a shows a top view of a section of a created, inventive display device 1.

In so doing, during the manufacturing the micro-openings A are created or incorporated on the surface facing a viewer O of the upper layer 4 with a percentage of less than 10% of the total surface O of the upper layer 4 facing the viewer. In the process, in the upper part of the display device 1 the micro-openings A are spaced further apart from one another than in the lower part. Consequently various distances can be realized and concurrently the target relating to the percentage of less than 10% of the total surface for the micro-openings can be ensured.

Figure 6B:
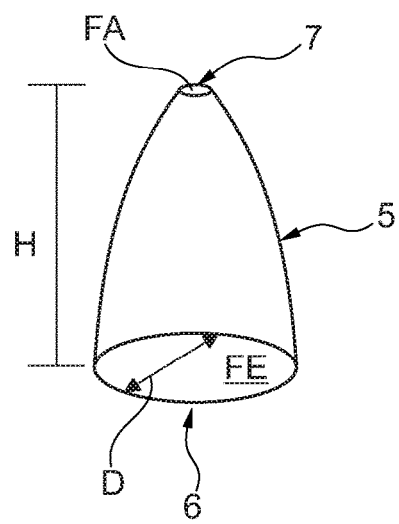
FIG. 6b shows a three-dimensional view of a beam shaping device 5 from FIGS. 1 to 5.

FIG. 6*b* is a three-dimensional view of a beam shaping device 5 from FIGS. 1 to 5.

In so doing, FIG. 6*b* shows schematically that the ratio of the area FE of the inlet 6 of the beam shaping device 5 or the ratio of the maximum area of the beam shaping device 5 to the area FA of the outlet 7 of the beam shaping device 5 is less than 1:25.

Furthermore FIG. 6*b* indicates that the ratio of the area FA exiting through the upper layer beam shaping device 5 to the area of the upper layer is less than 1:100.

It can also be seen from FIG. 6*b* that the distance H from inlet 6 to outlet 7 of the beam shaping device 5 in proportion to the maximum diameter D at the inlet 6 of the beam shaping device 5 is equal to 1:1.

In the process, the outlet 7 of the beam shaping device 5 has a diameter of less than 50 μm. An even smaller diameter is preferable.

FIGS. 7 to 11 show a second exemplary embodiment of a manufacturing method of a thin and substantially fracture resistant display device in various individual steps.

In so doing all of the steps of the second exemplary embodiment are identical to the first. However the beam shaping devices 5 are different. Therefore, the following text only covers the differences, without repeating the further explanations, which can be applied analogously from the first exemplary embodiment to the second.

Figure 7:
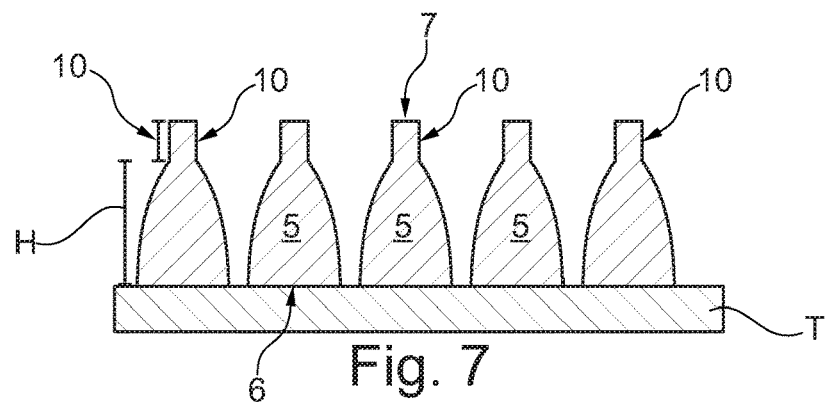
FIGS. 7 to 11 show a second exemplary embodiment of a manufacturing method of a thin and substantially fracture resistant display device in various individual steps.
Figure 8:
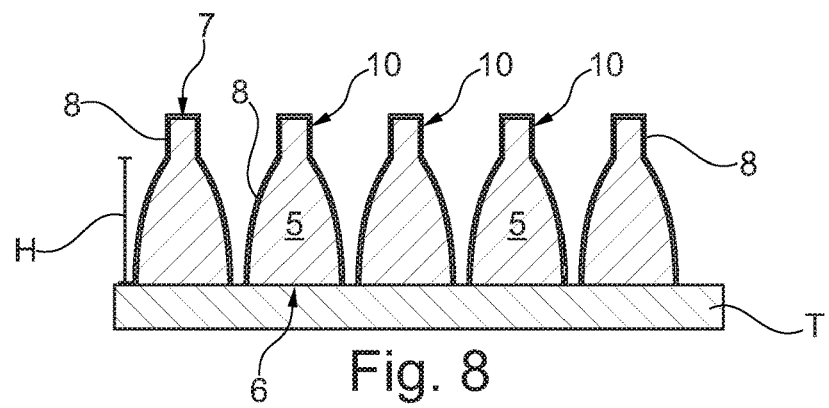
Figure 9:
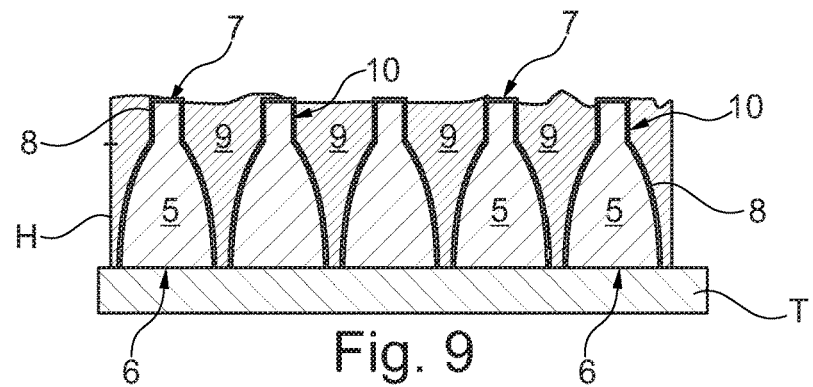

So is also, described in detail, the manufacturing step from FIG. 1 is identical to the manufacturing step according to FIG. 7, the manufacturing step from FIG. 2 is identical to the manufacturing step according to FIG. 8, the manufacturing step from FIG. 3 is identical to the manufacturing step according to FIG. 9, etc. All of the explanations, as already mentioned, about the respective corresponding steps can be transferred analogously or even identically from the first exemplary embodiment to the second.

The difference between the first and second exemplary embodiment is the embodiment of the beam shaping devices 5.

According to the second exemplary embodiment, in contrast to the beam shaping devices of the first exemplary embodiment, these have a sacrificial element 10 on the outlet side.

Said sacrificial element is configured to be cylindrical in the present example and extends one beam shaping device 5 upward, so that in total the upper layer 4 increases in thickness.

Of course the sacrificial elements 10 of the beam shaping devices 5 can take on further shapes. Thus, they can also be configured rectangular or conical. Furthermore, the sacrificial element 10 is fabricated from the same material as the previously described beam shaping devices 5 and hence they are preferably configured in one piece or one part with one another. The material can be a translucent material which can absorb and transmit light.

Analogous to FIG. 3, in FIG. 9 the upper layer 4 is fabricated by means of a generative production method, in particular by means of molding of a material. The molding or fabrication of the upper layer 4 features a filling of the intermediate spaces 9 between the beam shaping devices 5. As a result among other things the mechanical stability is increased.

In so doing the quantity of material used for filling, in particular plastic or metal, covers the beam shaping devices 5 at least on the surface facing the viewer O such that at least one region of the sacrificial element is free from material or the sacrificial element 10 is enclosed to a great extent with material.

Figure 10:
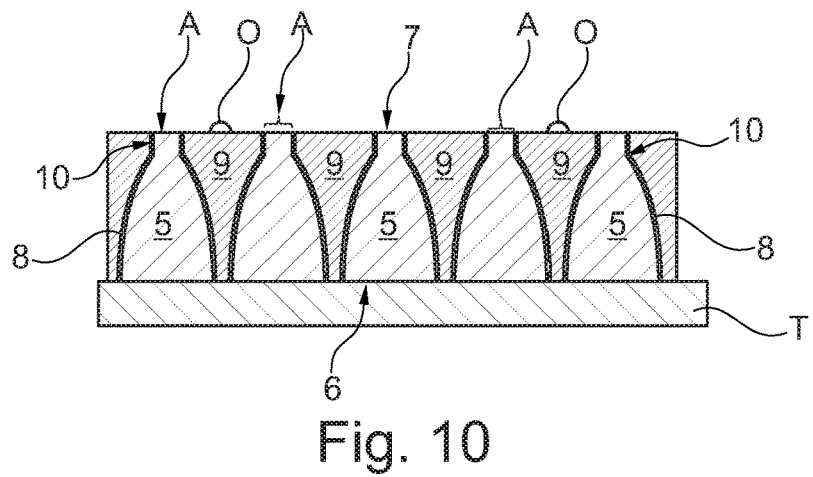

In the subsequent step according to FIG. 10, analogous to FIG. 4 a substantially plane surface facing the viewer O is created on the upper layer 4. In the process, in the forming of the substantially plane surface O an optical passage is created, so that light from the beam shaping devices 5 can enter and/or exit. As a result the beam shaping devices 5 are created at least partially or completely within the upper layer.

The forming of the substantially plane surface O comprises a processing of the surface facing the viewer O of the display device 1 by means of a material removing method, in particular by means of grinding and/or polishing. It is also possible by means of a laser and/or by means of machining, preferably by means of milling and/or boring, and/or by means of a chemical process, preferably by means of etching, and/or by means of polishing and/or grinding to generate a surface O or a surface layer.

In so doing the advantage of the sacrificial element 10 also comes to light. This is due to the fact that production tolerances in the forming of the beam shaping elements 5 together with the sacrificial elements 10 can be designed more generously, as a result of which Production costs can be lowered.

While in the case of the first exemplary embodiment after the molding it is necessary to grind exactly to the height of the beam shaping devices in order to obtain a maximum of light output, this is no longer necessary for the second exemplary embodiment due to the sacrificial elements 10. The height of the sacrificial elements 10 can be sacrificed for the abrasion without seeing losses in the light output for beam shaping devices 5. Hence in abrasion e.g. in the form of a grinding process a greater tolerance can be used in the abrasion. Furthermore, as a result of this less scrap is produced, and hence productivity is increased.

To express the above statements regarding FIG. 10 in different wording, in creating a plane surface O, micro-openings A are generated in the upper layer 4, wherein these micro-openings A make it possible for light at the outlet 7 formed by the sacrificial elements 10 to exit the beam shaping devices 5.

To summarize, for the step described in FIG. 10 it can be stated that the processing of the surface facing the viewer O comprises a generation of a common plane surface O, wherein the upper layer 4 and a plurality of beam shaping devices 3, in particular their outlets 7, are processed such that light can exit from the outlets 7 of the beam shaping devices 3. In so doing the outlets 7 are formed by sacrificial elements 10 of the beam shaping devices 5.

In general, it can also be stated here that the fabrication of the upper layer happens by means of a generative production method, wherein the fabrication of the upper layer 4 likewise comprises a forming of a further layer and/or at least one functional layer and/or the forming of the beam shaping devices 5.

Furthermore here too, as in the case of the first exemplary embodiment according to FIG. 4, after the processing of the surface facing the viewer O by generating a common plane surface the carrier T is removed. This is performed with the help of an abrasive procedure, in particular by means of grinding and/or polishing. Of course it is also possible here to remove the carrier T by means of a laser and/or by means of machining, preferably by means of milling and/or boring, and/or by means of a chemical process, preferably by means of etching, and/or by means of polishing and/or grinding.

Figure 11:
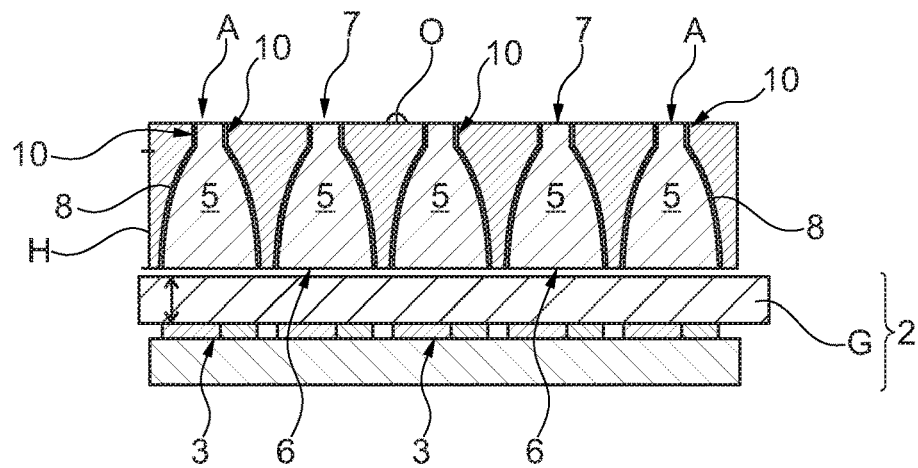

In the subsequent step—presented in FIG. 11—the display 2 is arranged on the upper layer 4 from FIG. 10 to form the thin and substantially fracture resistant display device 1. Please refer to our statements about FIG. 5.

FIGS. 12 to 17 show a third exemplary embodiment of a manufacturing method of a thin and substantially fracture resistant display device in various individual steps.

Figure 12:
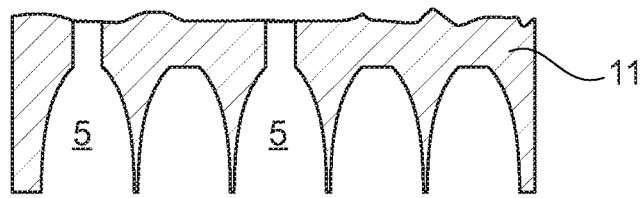
FIGS. 12 to 17 show a third exemplary embodiment of a manufacturing method of a thin and substantially fracture resistant display device in various individual steps.

In so doing in a first step, indicated in FIG. 12, a matrix 11 is created for a stamping tool and/or an injection molding tool. In order to show the variants from the previous two exemplary embodiments, i.e. beam shaping devices 5 with and without sacrificial element 10, simultaneously, in FIG. 12 or 13 both variants are presented. Two different embodiments for sacrificial elements 10 are also shown.

Figure 13:
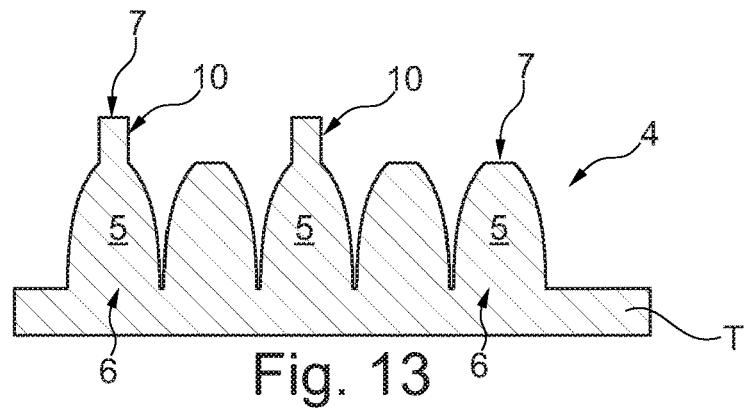

After the forming of a matrix, with the help of said matrix and by means of a nanoimprint and/or of a roller embossing methods and/or of an injection molding methods beam shaping devices 5, as shown in FIG. 12 or 13, are created with and without sacrificial element 10. In the process the beam shaping devices 5 are connected via a carrier T.

With reference to FIG. 13 the first, left sacrificial element 10 is an embodiment configured identically to the above described, second exemplary embodiment. By contrast, the second, right sacrificial element 10 has a conical shape tapering from bottom to top. Thus various shapes can be conceived and also implemented for sacrificial elements 10.

As already mentioned with respect to the two previous exemplary embodiments, one beam shaping device 5 in the third exemplary embodiment also has an inlet 6 and an outlet 7, wherein the outlet 7 can now be found on the sacrificial element 10.

Figure 14:
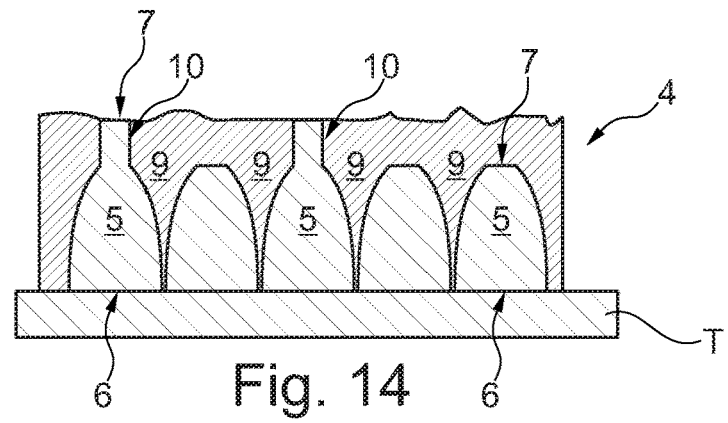

In FIG. 14 the upper layer 4 is further fabricated by means of galvanic application, wherein the intermediate spaces 9 between the beam shaping devices 5 are filled. With the help of this measure the mechanical stability is increased.

Furthermore the quantity of material used for filling, which in the present case is a metal, preferably titanium, now completely covers the beam shaping devices 5 along with sacrificial elements 10. As shown, in the case of galvanic application no substantially plane surface O is created on the upper layer 4.

Ideally, another step of the method can precede the filling of the intermediate spaces 9 by means of galvanic application. In this step preferably the surfaces of the beam shaping devices 5 are vaporized or sputtered with a light-reflecting metal. This allows the beam shaping devices 5 to concentrate the amount of light from the inlets 6 to the outlets 7, in order to reduce losses and conserve energy. The application of such a layer is described analogously for the first and second exemplary embodiments, however in connection with an electrically conductive material, wherein this material can also be configured to be light-reflecting, such as e.g. aluminum.

Figure 15:
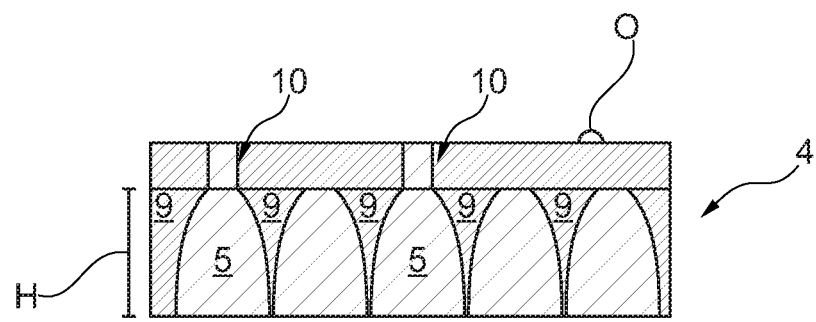

In a subsequent step—presented in FIG. 15—a substantially plane surface facing the viewer O is created on the upper layer 4. In the process, in the forming of the substantially plane surface an optical passage is created, so that light can exit from the sacrificial elements 10 or the outlets 7 of the beam shaping devices 5 or light can enter and/or exit from the beam shaping devices 5. As a result the beam shaping devices 5 are created at least partially or completely within the upper layer.

In addition the carrier T is removed. The forming of a substantially plane surface O facing the viewer and the removal of the carrier T is carried out by means of a reworking of the upper layer 4. In the process the reworking of the upper layer 4 is carried out by means of a laser and/or by means of machining, preferably by means of milling and/or boring, and/or by means of a chemical process, preferably by means of etching, and/or by means of polishing, in order to generate the upper layer 4 or a surface layer, if the upper layer 4 is composed of several layers.

Figure 16:
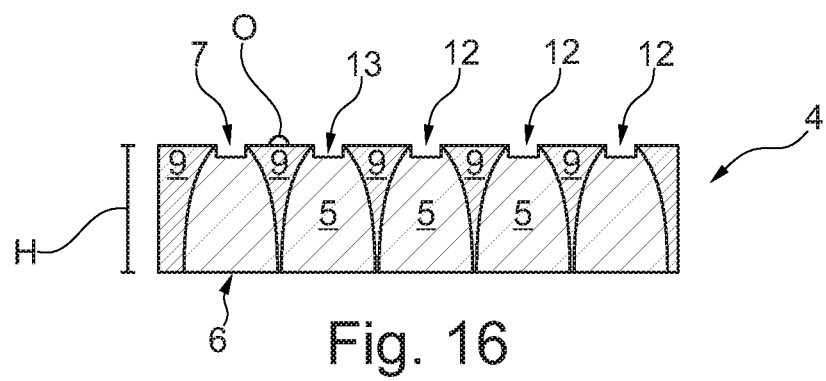

For the sake of simplicity in the subsequent step according to FIG. 16 the display of the sacrificial elements 10 is omitted. However, please note that the subsequent description also applies to beam shaping devices 5 with sacrificial elements 10.

According to FIG. 16 in the subsequent step according to FIG. 15 the upper layer 4 is reworked such that by means of etching recesses 11 are created at the outlets 7 of the beam shaping devices 5. In so doing prior to the etching process by means of a paint that can be applied and exposed and by means of a mask and a subsequent exposure process regions are defined on the upper layer 4 that are supposed to be removed or protected during etching. In other words, this process is configured analogously to that of microchip manufacturing.

In the created recesses 12, which are arranged on each outlet 7 of the beam shaping devices 5, one diffusion element 13 each, is designed as a diffuser. It is also possible instead of or in addition to position a collimator in a recess 11.

In so doing the diffusion elements 13 can be created by an application by means of a spackling process, in which a spackling compound penetrates into the recesses 12 formed by the micro-openings.

Figure 17:
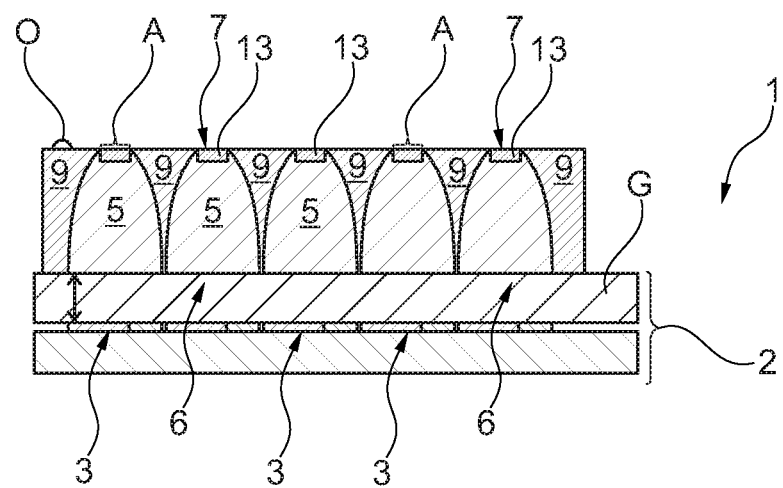

After the upper layer 4 has been completed, in a further step—presented in FIG. 17—it can be arranged on the display 2 for completion of the thin and substantially fracture resistant display device 1.

To this end the upper layer 4 is arranged on a glass substrate G of the display above the light-emitting luminous areas 3 of the display 2. The arrangement can for example be supported with a bonding agent, so that the upper layer 4 is connected to the display 2.

More precisely, the micro-passages formed in the upper layer or the beam shaping devices 5 forming the micro-passages with their inlet 6 are arranged over light-emitting luminous areas 3 of the display 2 or above light-emitting luminous areas 3 of the display 2. As a result the outlets 7 of the beam shaping devices 5 are arranged on the surface facing a viewer O of the upper layer 4.

The display 2 has OLEDs or a micro display as light-emitting luminous areas 3. Therefore the OLEDs or the micro display outside of the micro-passages, formed by the beam shaping devices 5 within the upper layer 4 are arranged such that the light generated from the luminous areas 3 can pass through the upper layer 4. In other words, light from the light-emitting luminous areas 3 enters into the inlets 6 if a beam shaping device 5 and exits from their outlets 7. Hence—as already indicated—the micro-passages or the beam shaping devices 5 forming the micro-passages are used to let light pass, so that generated light of the light-emitting luminous areas 3 of the display 2 forms micro-openings A in the surface O facing a viewer.

In the following, further embodiments of the inventive method are briefly outlined. These statements can be applied to all of the presented exemplary embodiments.

Thus, it is for example possible that the fabrication of the upper layer 4 comprises a forming of a further layer and/or at least one functional layer and/or in addition to the forming of beam shaping devices 5. In the process, a solar layer can be created for generating power as at least one functional layer and/or a touch-sensitive layer can be created for acquiring input and/or a pressure-sensitive layer can be created for recording pressure and/or a temperature-sensitive layer can be created for measuring a temperature and/or a capacitive layer can be created for measuring a capacity as at least one functional layer.

In the process, it is conceivable that in forming of the at least one functional layer at least one sensing element is introduced into the functional layer, wherein preferably the at least one sensing element can be configured as a touch sensor and/or as a temperature sensor and/or as a pressure sensor and/or as a capacitive sensor.

It is also possible that in forming of the beam shaping devices 5 at least one sensing element is arranged between two beam shaping devices. Alternatively or in addition the display or its light-emitting side can also have at least one sensing element. In addition, it is conceivable that at least one sensing element is applied between the display and the upper layer.

The at least one sensory element can be a sensor, in particular a two-dimensional and/or three-dimensional sensor, preferably an image sensor and/or a touch-sensitive and/or a pressure-sensitive and/or gas-sensitive sensor, in particular a piezo element.

Furthermore, it is not compulsory to create the upper layer 4 on a carrier T. It is also possible to arrange the upper layer 4 directly on the glass substrate G or the display 2 luminous area 3. As a result, an even thinner and hence lighter display device can be created.

Regarding all of the aforementioned exemplary embodiments and their possible variants, it should be noted that they can, of course be combined with one another. Such combinations arise in particular from the general part of the description.

LIST OF REFERENCES

1 Display device
2 Display
3 Luminous area
4 Upper layer
5 Beam shaping device
6 Inlet
7 Outlet
8 Electrically conductive material
9 Intermediate space
10 Sacrificial element
11 Matrix
12 Recess
13 Diffusion element
A Micro-opening
T Carrier
G Glass substrate
FA Area of the outlet
FE Area of the inlet
D Diameter at the inlet
H Distance

The invention claimed is:

1. A thin display device with a display, the display comprising a light-emitting layer having a plurality of light sources and an upper layer arranged over the light emitting layer, the upper layer having a display surface facing a viewer, wherein micro-passages are formed in the upper layer extending from the light emitting layer to micro-openings in the display surface for allowing transmission of light generated by the light sources from the light emitting layer to said microopenings in the display surface facing a viewer, wherein at least one functional layer is formed on the upper layer, the functional layer comprising at least one of:
   a solar layer for generating power;
   a touch-sensitive layer for acquiring input;
   a pressure-sensitive layer for recording pressure;
   a temperature-sensitive layer for measuring a temperature; and
   a capacitive layer for measuring a capacity.

2. A thin display device with a display, the display comprising a light-emitting layer having a plurality of light sources and an upper layer arranged over the light emitting layer, the upper layer having a display surface facing a viewer, wherein micro-passages in the form of beam shaping devices are formed in the upper layer extending from the light emitting layer to micro-openings in the display surface for allowing transmission of light generated by the light sources from the light emitting layer to said micro-openings in the display surface facing a viewer, wherein a ratio of an area of an inlet of said beam shaping device and an area of an outlet of said beam shaping device is less than or equal to 1:25.

3. A thin display device with a display, the display comprising a light-emitting layer having a plurality of light sources and an upper layer arranged over the light emitting layer, the upper layer having a display surface facing a viewer, wherein micro-passages are formed in the upper layer extending from the light emitting layer to micro-openings in the display surface for allowing transmission of light generated by the light sources from the light emitting layer to said micro-openings in the display surface facing a viewer, wherein the upper layer between micro-passages comprises a material adapted to improve the reception of radio signals for antennas.

4. A thin display device with a display, the display comprising a light-emitting layer having a plurality of light sources and an upper layer arranged over the light emitting layer, the upper layer having a display surface facing a viewer, wherein micro-passages in the form of beam shaping devices are formed in the upper layer extending from the light emitting layer to micro-openings in the display surface for allowing transmission of light generated by the light sources from the light emitting layer to said micro-openings in the display surface facing a viewer, the at least one beam shaping device comprising at least partially a translucent material, wherein the upper layer between micro-passages comprises at least one element to measure noise or emit noise.

5. A thin display device with a display, the display comprising a light-emitting layer having a plurality of light sources and an upper layer arranged over the light emitting layer, the upper layer having a display surface facing a viewer, wherein micro-passages in the form of beam shaping devices are formed in the upper layer extending from the light emitting layer to micro-openings in the display surface for allowing transmission of light generated by the light sources from the light emitting layer to said micro-openings in the display surface facing a viewer, the at least one beam shaping device comprising at least partially a translucent material, wherein the upper layer between micro-passages comprises at least one actuator including any one or more of a micromotor, a micro-melt element, a micro-electromagnetic or magnetic element, a micro-air compression or micro-hydraulic element, a shape memory material, and an antenna.

* * * * *